(12) United States Patent
Mehawej et al.

(10) Patent No.: US 10,589,035 B2
(45) Date of Patent: Mar. 17, 2020

(54) INJECTION DEVICE

(71) Applicant: Antares Pharma, Inc., Ewing, NJ (US)

(72) Inventors: John Pierre Mehawej, Robbinsdale, MN (US); Bryan James Sarkinen, St. Louis Park, MN (US)

(73) Assignee: Antares Pharma, Inc., Ewing, NJ (US)

( * ) Notice: Subject to any disclaimer, the term of this patent is extended or adjusted under 35 U.S.C. 154(b) by 120 days.

(21) Appl. No.: 15/567,139

(22) PCT Filed: Apr. 18, 2016

(86) PCT No.: PCT/US2016/028117
§ 371 (c)(1),
(2) Date: Oct. 17, 2017

(87) PCT Pub. No.: WO2016/172048
PCT Pub. Date: Oct. 27, 2016

(65) Prior Publication Data
US 2018/0093045 A1 Apr. 5, 2018

Related U.S. Application Data

(60) Provisional application No. 62/149,862, filed on Apr. 20, 2015.

(51) Int. Cl.
*A61M 5/32* (2006.01)
*A61M 5/20* (2006.01)

(52) U.S. Cl.
CPC .......... *A61M 5/326* (2013.01); *A61M 5/2033* (2013.01); *A61M 5/3204* (2013.01);
(Continued)

(58) Field of Classification Search
CPC .. A61M 5/326; A61M 5/2033; A61M 5/3204; A61M 5/3245; A61M 2005/2013; A61M 2005/3247
See application file for complete search history.

(56) References Cited

U.S. PATENT DOCUMENTS 5,620,421 A * 4/1997 Schmitz .............. A61M 5/2033
604/135
5,658,259 A * 8/1997 Pearson .............. A61M 5/2033
604/136

(Continued)

OTHER PUBLICATIONS

International Search Report and Written Opinion dated Jul. 26, 2016 for International Patent Application No. PCT/US2016/028117, 2 pages.

*Primary Examiner* — Nathan R Price
*Assistant Examiner* — Melissa A Snyder
(74) *Attorney, Agent, or Firm* — Morgan, Lewis & Bockius LLP

(57) ABSTRACT

An injection device for injecting medicament in a patient includes a syringe coupled to a housing and radially retained by a retaining rib. A needle guard is slideably coupled to the housing and spring biased in a distal direction by a return spring. A ram is slideably coupled to the housing and spring biased in the distal direction by a main spring. An initial position is defined by a retaining arm being disposed in the longitudinal path of the ram preventing firing. A released position is defined by the retaining arm being clear from the longitudinal path of the ram allowing the ram to extend distally. A locked position is defined by the retaining arm being disposed in the longitudinal path of the ram and a lock arm of the ram being disposed in the longitudinal path of the needle guard preventing the needle guard from being retracted.

21 Claims, 7 Drawing Sheets

(52) U.S. Cl.
CPC ... *A61M 5/3245* (2013.01); *A61M 2005/2013* (2013.01); *A61M 2005/3247* (2013.01)

(56) References Cited

U.S. PATENT DOCUMENTS

| | | | | |
|---|---|---|---|---|
| 2005/0020979 | A1* | 1/2005 | Westbye | A61M 5/2033 604/151 |
| 2007/0265568 | A1* | 11/2007 | Tsals | A61M 5/2033 604/136 |
| 2008/0268682 | A1* | 10/2008 | Ting | G06K 13/08 439/159 |
| 2013/0018313 | A1* | 1/2013 | Kramer | A61M 5/2033 604/131 |
| 2013/0296795 | A1* | 11/2013 | Ekman | A61M 5/2033 604/197 |
| 2014/0135303 | A1* | 5/2014 | Wotton | A61K 9/0019 514/180 |
| 2014/0330214 | A1* | 11/2014 | Olson | A61M 5/20 604/189 |

* cited by examiner

INJECTION DEVICE

CROSS-REFERENCE TO RELATED APPLICATIONS

This application is a U.S. National Stage filing of International Patent Application No. PCT/US2016/028117 filed Apr. 18, 2016, which claims the benefit of U.S. Provisional Patent Application No. 62/149,862 filed Apr. 20, 2015 entitled "Injection Device", each of which is incorporated by reference herein in its entirety.

FIELD OF THE INVENTION

The present invention generally relates to an injection device and, in some embodiments, to an auto-injection device that has a reduced number of components.

BACKGROUND OF THE INVENTION

Injection devices for injection of medicaments into a patient are generally known. Such devices include, for example, traditional hypodermic needle syringes that contain a stock of medicament therein. Upon insertion of the needle under the patient's skin at an injection location, the medicament is forced out of the syringe and through the needle by depression of a plunger mechanism.

Self-injectors or auto-injectors like the ones disclosed in U.S. Pat. Nos. 4,553,962 and 4,378,015, and PCT Patent Application Publications WO 95/29720 and WO 97/14455 are configured to inject medicament at a rate and in a manner similar to hand-operated hypodermic syringes.

These injectors often are made for a single use, or alternatively to be refilled after each injection. Some refillable injectors can be refilled with a desired dosage to be injected. Upon injection, the entire loaded dosage is injected.

BRIEF SUMMARY OF THE INVENTION

In one embodiment there is an injection device for injecting medicament in a patient comprising: a housing having at least one retaining arm and at least one retaining rib; a syringe coupled to the housing and radially retained relative to the housing by the at least one retaining rib, the syringe having a needle and a piston; a needle guard slideably coupled to the housing and spring biased in a distal direction relative to the housing by a return spring; a ram slideably coupled to the housing and spring biased in the distal direction relative to the housing by a main spring, the ram having a rod coupled to the piston, the ram having at least one lock arm; an initial position defined by the at least one retaining arm being disposed in the longitudinal path of the ram preventing firing of the ram; a released position defined by the at least one retaining arm being clear from the longitudinal path of the ram allowing the ram to extend distally relative to the housing; and a locked position defined by the at least one retaining arm being disposed in the longitudinal path of the ram and the at least one lock arm being disposed in the longitudinal path of the needle guard preventing the needle guard from being retracted relative to the housing.

In one embodiment, the needle guard includes at least one window and the at least one retaining arm extends through the at least one window. In one embodiment, the needle guard extends between the at least one retaining arm and the housing in the initial and locked positions and the at least one window is aligned with the at least one retaining arm in the released position. In one embodiment, the at least one retaining rib is integral with the housing. In one embodiment, the at least one retaining rib includes four retaining ribs. In one embodiment, the at least one retaining rib includes a radially extending stop configured to abut a bottom surface of a flange of the syringe. In one embodiment, the at least one lock arm is integral with the ram. In one embodiment, the at least one lock arm includes two diametrically opposed lock arms. In one embodiment, the at least one lock arm extends distally further than the rod.

In one embodiment, the at least one retaining arm is integral with the housing. In one embodiment, the at least one retaining arm includes two diametrically opposed retaining arms. In a further embodiment, the injection device comprises a cap. In one embodiment, the cap includes an extension that extends through the main spring. In one embodiment, the return spring abuts against the at least one retaining rib. In one embodiment, the housing includes at least one hook configured to abut against a portion of the needle guard in the released position and radially flex the at least one lock arm as the lock arm extends distally. In one embodiment, the at least one retaining arm includes a cantilever arm that extends in a proximal direction. In one embodiment, the at least one retaining arm includes a radial projection having a sloped surface that abuts a sloped surfaced of the ram in the initial position. In one embodiment, the ram includes at least one window configured to couple with the at least one retaining arm in the locked position. In one embodiment, the injection device consists of the housing, the syringe, the needle, the ram, the needle guard, the return spring, the main spring, and a cap. In one embodiment, the at least one lock arm includes two diametrically opposed lock arms and the at least one retaining arm includes two diametrically opposed retaining arms, each of the two lock arms being circumferentially spaced from each of the two retaining arms.

In another embodiment, there is an auto-injector device consisting of: a syringe having a needle; a housing retaining the syringe; a return spring; a needle guard slidably coupled to the housing and spring biased relative to the housing by the return spring; a main spring; a ram slidably coupled to the housing and spring biased relative to the housing by the main spring; and a cap coupled to a proximal end of the housing. In one embodiment, a portion of the ram and a portion of the needle guard slide between the syringe and the housing during use.

BRIEF DESCRIPTION OF THE SEVERAL VIEWS OF THE DRAWINGS

The following detailed description of embodiments of the injection device will be better understood when read in conjunction with the appended drawings of an exemplary embodiment. It should be understood, however, that the invention is not limited to the precise arrangements and instrumentalities shown.

In the drawings.

DETAILED DESCRIPTION OF THE INVENTION

Figure 1:
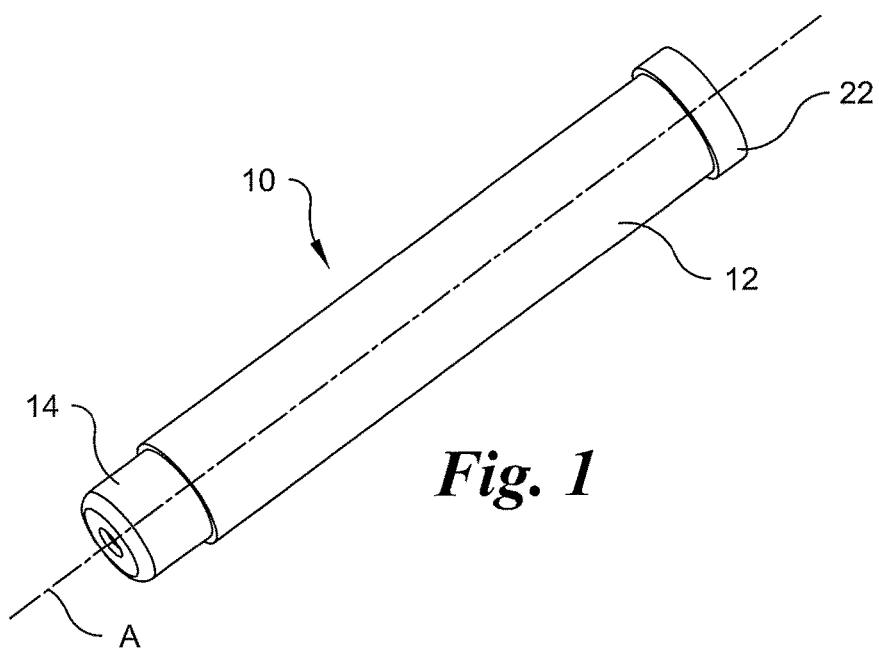
FIG. 1 is a perspective view of an injection device in accordance with an exemplary embodiment of the present invention.

Referring to the drawings in detail, wherein like reference numerals indicate like elements throughout, there is shown in FIGS. 1-11B an injection device, generally designated 10, an exemplary embodiment of the present invention. Various embodiments of the injection device are described in further detail below in reference to the exemplary embodiment shown in the figures.

Auto-injectors allow for the safe and convenient delivery of medicament to a patient. Typical auto-injectors allow for automatic triggering of the firing mechanism upon insertion of the needle into the patient, delivery of the medicament, and automatic covering of the needle upon removal of the needle from the patient. In order to achieve this functionality, auto-injectors are typically comprised of numerous parts, resulting in complex interactions and requiring precise tolerances for each part. Such auto-injectors typically require complicated assembly steps. In some embodiments, the injection device 10 is configured to reduce the number of parts thereby simplifying assembly and allowing for a greater range of acceptable dimensional tolerances for each part.

As discussed in further detail below, the injection device 10 may include an initial position (FIGS. 6A-6B) where the ram 16 is retained from being fired, a released position (FIGS. 8A-8C) where the ram 16 is released and advanced distally relative to the housing 12, and a locked position (FIGS. 11A-11B) where the needle guard 14 extends distally past the end of the needle 18 and is prevented from being retracted relative to the housing 12.

Figure 2:
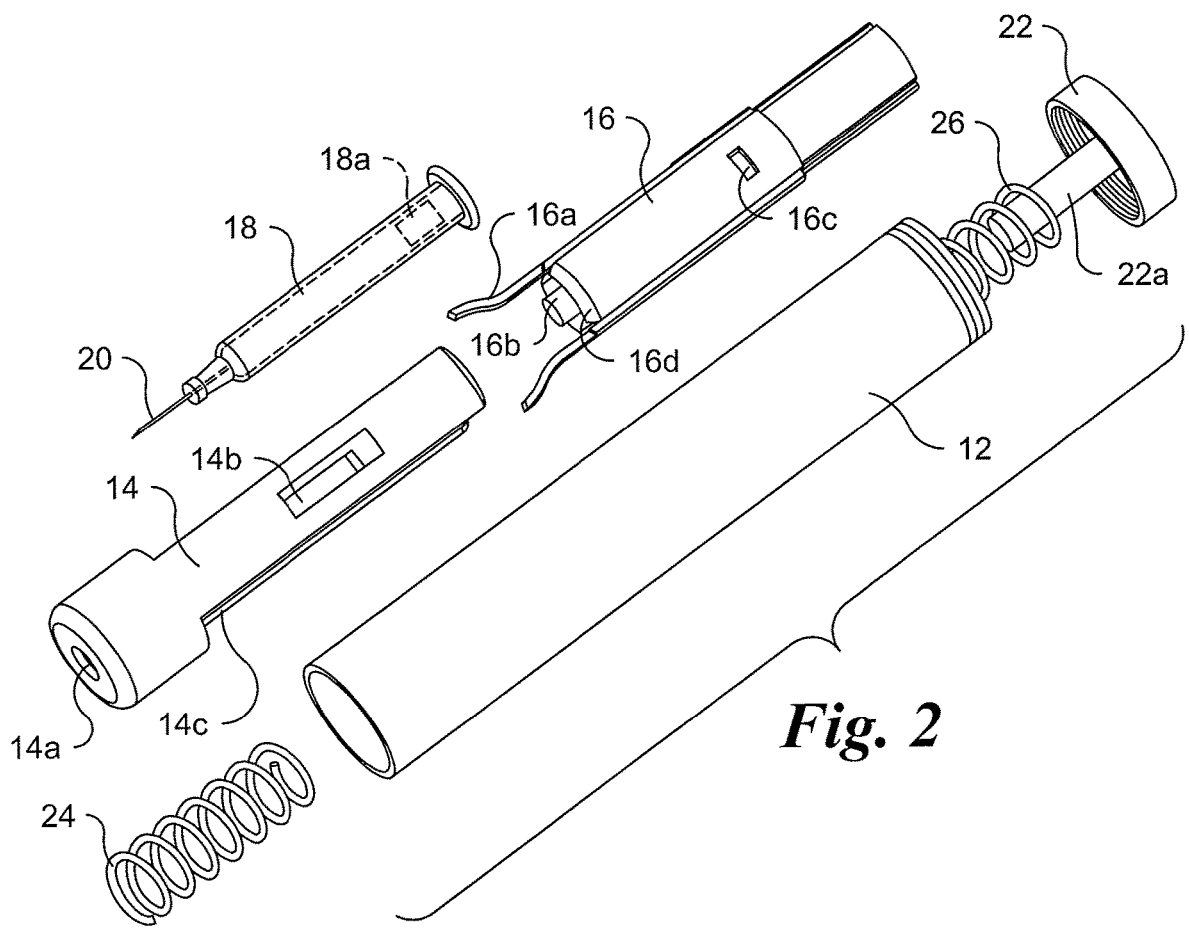
FIG. 2 is an exploded view of the injection device of FIG. 1.

Referring to FIGS. 1-2, the injection device 10 may be configured to house, actuate and protect the syringe 18 during storage and usage. The syringe 18 may be filled with a medicament and sealed at a proximal end with a slideable piston 18a. The syringe 18 may include a needle 20. The needle 20 may be pre-staked to the syringe 18 such that the syringe 18 and needle are inserted together and as a single component during assembly. Overall, the injection device 10 may include a housing 12, a needle guard 14, a ram 16, a syringe 18 having a needle 20, a cap 22, a return spring 24 (see FIG. 5A), and a main spring 26 (see FIG. 5C). In some embodiments, the injection device 10 consists of only these seven components. In one embodiment, the injection device 10 consists of a maximum of four plastic components (e.g., a housing 12, a needle guard 14, a ram 16, and a cap 22), two springs, and the syringe 18. In other embodiments, there may be additional or fewer components.

As described in further exemplary embodiments below, the injection device 10 may be configured such that the needle guard 14, the housing 12 and the ram 16 are configured to interact with one another to expose and protect the needle 20 without the need for additional components therebetween. The housing 12 may include one or more radially inwardly projecting features that interact with the needle guard 14 and the ram 16 to control the movement of the needle guard 14 and the ram 16 relative to the housing 12. In some embodiments, the position of the needle guard 14 relative to a projection of the housing 12 controls the position of the ram 16 relative to the housing 12 and/or the position of the ram 16 relative to a projection of the housing 12 controls the position of the needle guard 14 relative to the housing 12.

Each component may be comprised of any suitable material. In one embodiment, the housing 12, the needle guard 14, the ram 16, and the cap 22 are comprised of plastic such as acrylonitrile butadiene styrene (ABS), polycarbonate, polypropylene, polysulfone, polyether ether ketone (PEEK), nylon, polyethylene, acrylic, poly(vinyl chloride) (PVC), and/or polystyrene. The plastic components may be manufactured by injection-molding. In other embodiments, the plastic components are manufactured using an additive manufacturing process also referred to as 3D printing. The return spring 24 and the main spring 26 may be comprised of a high carbon spring wire known as music wire. The syringe 18 may be comprised of glass or plastic.

The housing 12 may be configured to be grasped and actuated with one hand of a user. The housing 12 may have a circular cross sectional shape. In other embodiments, the housing 12 may have any desired cross sectional shape for being grasped by a user such as oval, triangular or square. The housing 12 may extend along a longitudinal axis A between the cap 22 at the proximal end (i.e., the end furthest from the patient) and a needle guard 14 at the distal end (i.e., the end closest to the patient). The cap 22 may be coupled to the proximal end of the housing 12 by using a helical thread. In other embodiments, the cap 22 is coupled to the housing 12 by a snap fit or by using a fastener. In other embodiments, the cap 22 is integrally attached to the housing 12 by welding or through additive manufacturing.

Referring to FIGS. 2-4B, the housing 12 supports and retains the syringe 18; and the needle guard 14 and the ram 16 are slideably coupled to the housing 12. The housing 12 may include at least one radially inwardly projecting feature that interacts with the needle guard 14 and/or the ram 16. In one embodiment, the housing 12, includes three sets of projections that interact with the needle guard 14 and/or the ram 16. The inwardly projecting features may include at least one retaining arm 12b and at least one retaining rib 12c (see FIGS. 4A-4B). The at least one retaining arm 12b and the at least one retaining rib 12c may each extend radially inwardly from an inner surface of the housing 12. In one embodiment, the at least one retaining arm 12b and the at least one retaining rib 12c are integrally formed with the housing 12.

The retaining ribs 12c may be provided to hold the syringe 18 in place relative to the housing 12. In one embodiment, the retaining ribs 12c allow for the housing 12 to be radially spaced from the syringe 18 and allow for portions of the needle guard 14 and the ram 16 to slide between the syringe 18 and the inner wall of the housing 12. In one embodiment, the at least one retaining rib 12c includes four retaining ribs 12c. In one embodiment, there are two retaining ribs 12c disposed between each of the retaining arms 12b. One or more of the retaining ribs 12c may include a portion that abuts a side of the syringe 18 to prevent the syringe 18 from moving radially relative to the housing 10. One or more of the retaining ribs may include a radially extending stop 12d configured to abut a bottom surface of a flange of the syringe 18 preventing the syringe 18 from moving distally relative to the housing 10. In one embodiment, each retaining rib 12c abuts both the side of the syringe 18 and the bottom surface of the flange of the syringe 18. In other embodiments, certain retaining ribs 12c only abut the side of the syringe 18 and other retaining ribs 12c only abut the bottom surface of the flange of the syringe 18. In one embodiment, the return spring 24 abuts against the bottom surface of the retaining ribs 12c and extends to a distal end of the needle guard 14.

The at least one retaining arm 12b may include two diametrically opposed retaining arms. In one embodiment, the at least one retaining arm 12b includes a cantilever arm that extends in a proximal direction and is configured to radially flex outwardly toward the inner surface of the housing. The at least one retaining arm 12b, may include a radial projection having a sloped surface that abuts a sloped surfaced 16d of the ram 16 in the initial position. In one embodiment, the ram 16 includes at least one window 16c (see FIG. 9B) configured to couple with the at least one retaining arm 12b in the locked position.

Figure 3A:
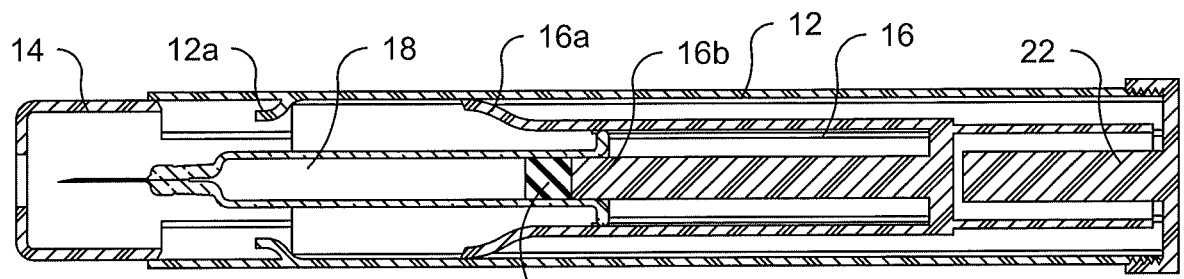
FIG. 3A is a first side cross sectional view of the injection device of FIG. 1.
Figure 3B:
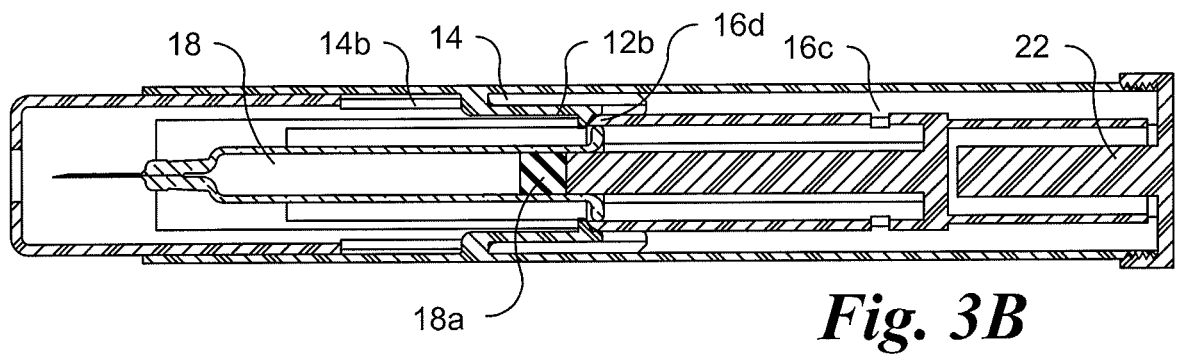
FIG. 3B is a second side cross sectional view of the injection device of FIG. 1 taken 90 degrees from the first side cross sectional view of FIG. 3A.
Figure 4A:
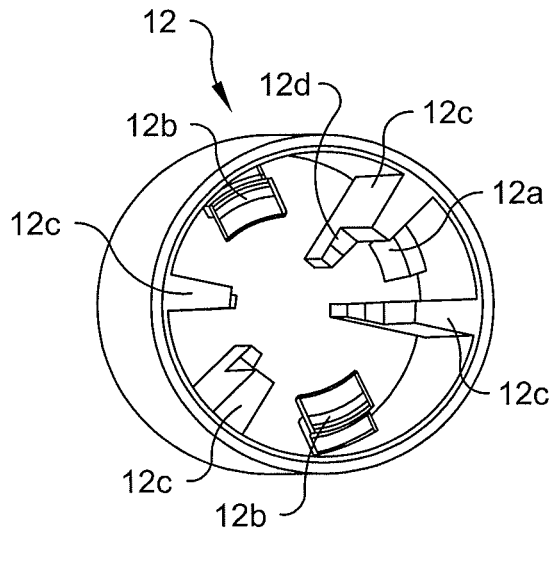
FIG. 4A is a perspective view of an interior of the housing of the injection device of FIG. 1 taken from a proximal end of the housing.
Figure 4B:
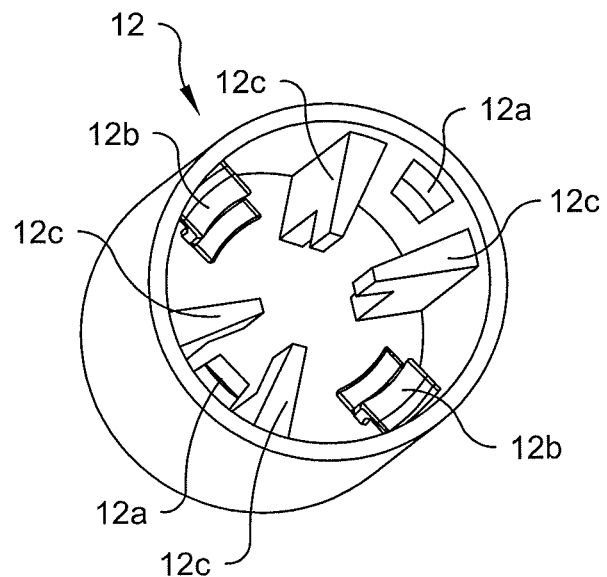
FIG. 4B is a perspective view of an interior of the housing of the injection device of FIG. 1 taken from a distal end of the housing.
Figure 5A:
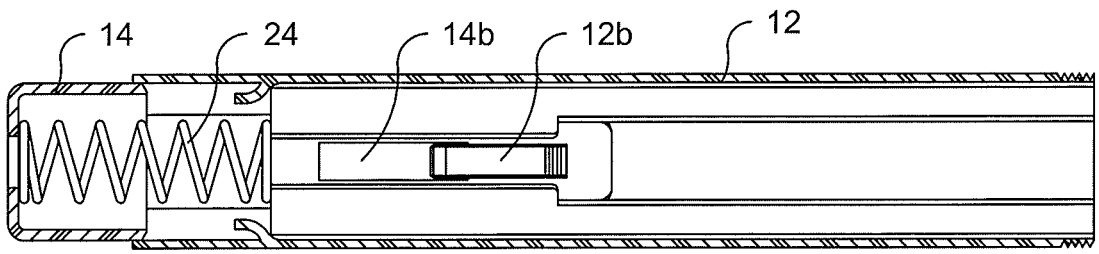
FIG. 5A is a cross sectional view of the injection device of FIG. 1 showing the needle guard and spring inserted into the housing during assembly.

Referring to FIGS. 2-3B, the needle guard 14 may be slideably coupled to the housing 12 and spring biased in a distal direction relative to the housing 12 by the return spring 24 (see FIG. 5A). In one embodiment, the return spring 24 is a helical compression spring. In other embodiments, the return spring 24 may be any preferred biasing member. The needle guard 14 may include at least one window 14b. In one embodiment, the at least one retaining arm 12b extends through the at least one window 14b. The retaining arm 12b may be configured to limit the distance that the needle guard 14 may extend distally relative to the housing 12. In some embodiments, the retaining arm 12b is configured to limit the distance that the needle guard 14 may be retracted and therefore control the depth of insertion of the needle 20. The needle guard 14 may also be configured to control that the injection of the medicament occurs when the needle 20 is at the correct depth of insertion. In one embodiment, the needle guard 14 extends between the at least one retaining arm 12b and the housing 12 in the initial and locked positions and the at least one window 14b aligns with the at least one retaining arm 12b in the released position.

Figure 5B:
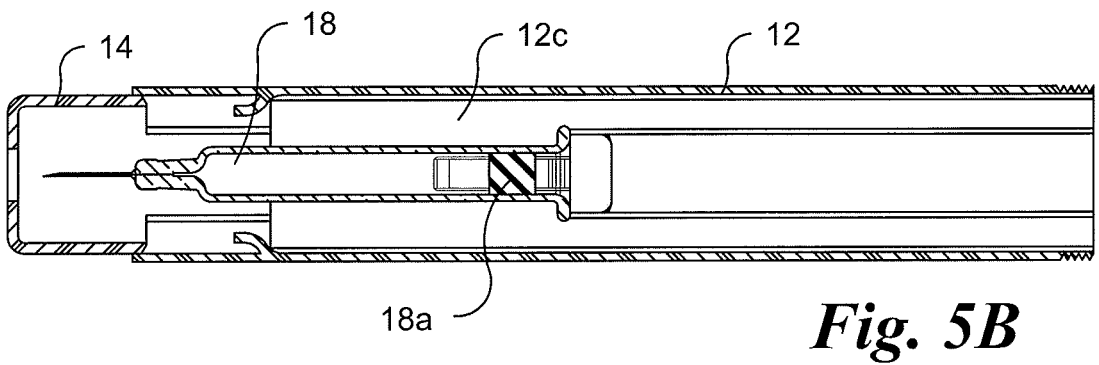
FIG. 5B is a cross sectional view of the injection device of FIG. 1 showing the syringe inserted into the housing during assembly.
Figure 5C:
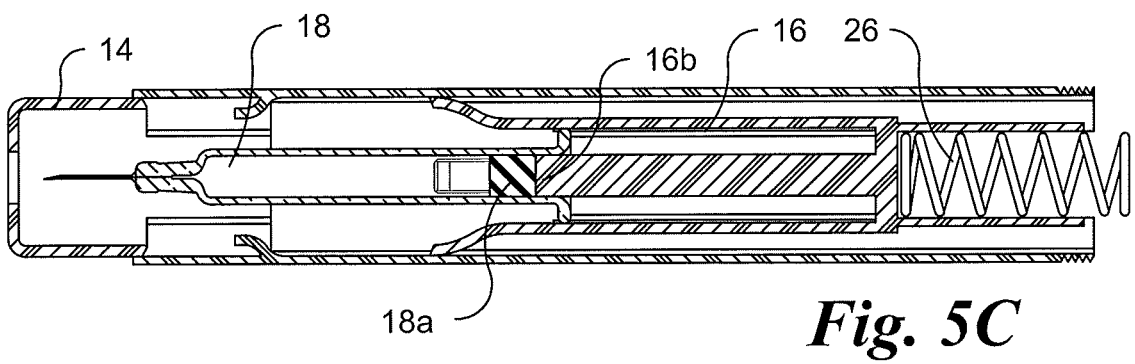
FIG. 5C is a cross sectional view of the injection device of FIG. 1 showing the ram inserted and spring into the housing during assembly.

The ram 16 may be slideably coupled to the housing 12 and spring biased in the distal direction relative to the housing 12 by the main spring 26 (see FIG. 5C). The ram 16 may include a rod 16b configured to urge the piston 18a through the syringe. The ram 16 may include at least one lock arm 16a. In one embodiment, the at least one lock arm 16a is integral with the ram 16. In one embodiment, the at least one lock arm 16a includes two diametrically opposed lock arms 16a. In one embodiment, the at least one lock arm 16a extends distally further than the rod 16b. In one embodiment, the at least one lock arm 16a includes two diametrically opposed lock arms 16a and the at least one retaining arm 12b includes two diametrically opposed retaining arms 12b, each of the two lock arms 16a being circumferentially spaced from each of the two retaining arms 12b.

The housing 12 may include at least one hook 12a configured to abut against a portion of the needle guard 14 in the released position and radially flex the at least one lock arm 16a as the lock arm 16a extends distally over the at least one hook 12a.

The cap 22 may include an extension 22a that extends through the main spring 26. The extension 22a may prevent the main spring 26 from buckling.

Referring to FIG. 5A, during an exemplary assembly of the injection device 10, the return spring 24 may be inserted into the end of the needle guard 14 or the distal end of the housing 12 and the proximal end of the needle guard 14 may be inserted in the distal end of the housing 12. The needle guard 14 may be inserted into the housing such that the retaining arms 12b extend through the respective window 14b of the needle guard 14.

Referring to FIG. 5B, the syringe 18 may be inserted into the proximal end of the housing until the bottom surface of the flange of the syringe engages with the retaining ribs 12c.

Referring to FIG. 5C, the ram 16 may be inserted into the proximal end of the housing until the rod 16a of the ram 16 abuts against the piston 18a of the syringe. The main spring 26 may be inserted into the proximal end of the ram 16.

Figure 5D:
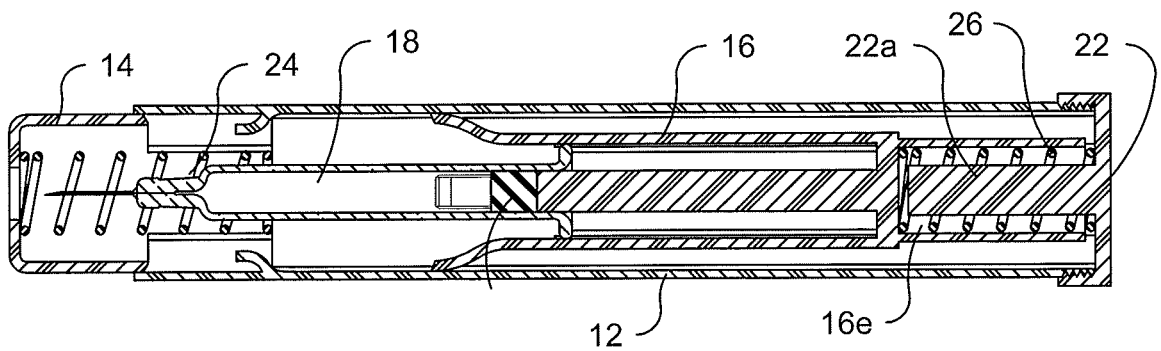
FIG. 5D is a cross sectional view of the injection device of FIG. 1 showing the cap coupled to the housing during assembly.

Referring to FIG. 5D, the cap 22 may be coupled to the proximal end of the housing 12 to retain the main spring 26.

Figure 6A:
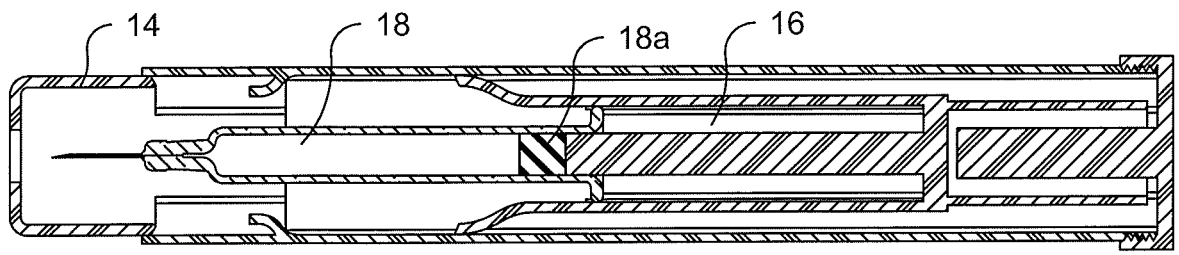
FIG. 6A is a cross sectional view of the injection device of FIG. 1 shown in an initial position and with the springs omitted for clarity.
Figure 6B:
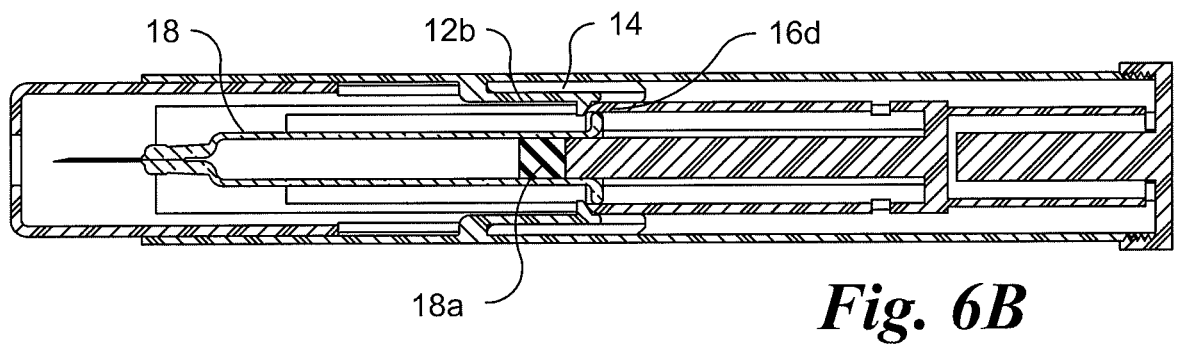
FIG. 6B is a cross sectional view of the injection device of FIG. 1 shown in an initial position and taken 90 degrees from the cross sectional view of FIG. 6A.

Referring to FIGS. 6A-6B, during an exemplary use of the injection device 10, the initial position may be defined by the at least one retaining arm 12b being disposed in the longitudinal path of the ram 16 preventing firing of the ram 16. In the initial position, a portion of the needle guard 14 may extend between the retaining arm 12b and the inner wall of the housing 12 to prevent the retaining arm 12c from flexing and moving out of the longitudinal path of the ram 16.

Figure 7A:
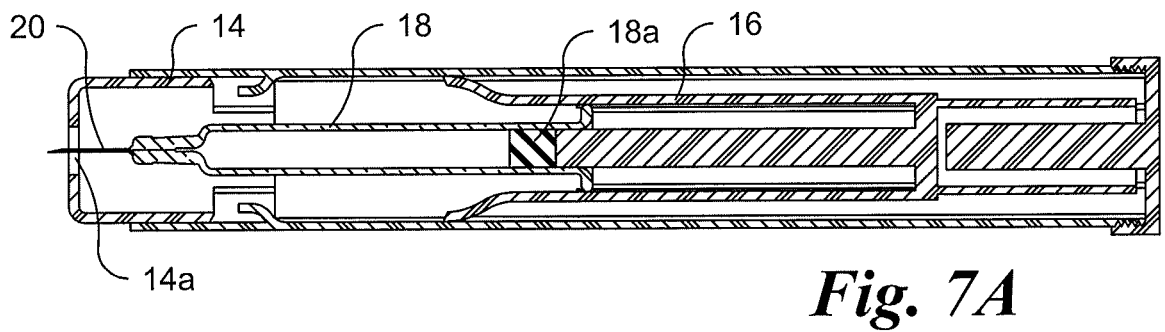
FIG. 7A is a cross sectional view of the injection device of FIG. 1 shown with the needle guard partially retracted and with the springs omitted for clarity.
Figure 7B:
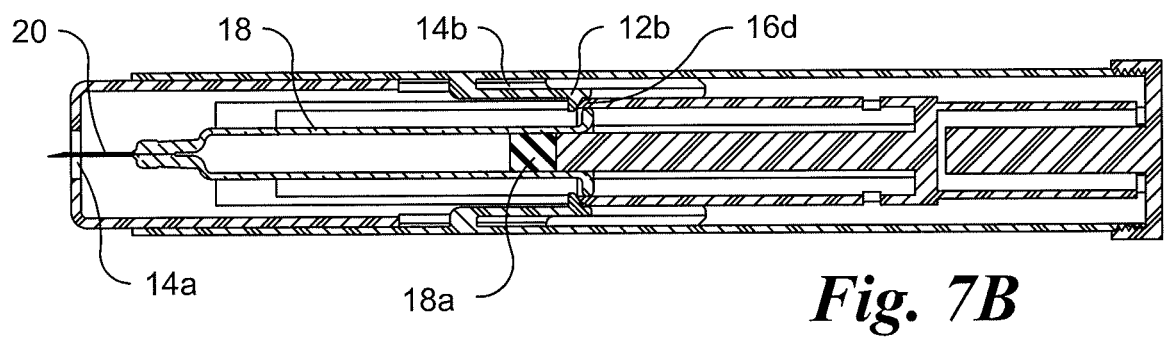
FIG. 7B is a cross sectional view of the injection device of FIG. 1 shown with the needle guard partially retracted and taken 90 degrees from the cross sectional view of FIG. 7A.

Referring to FIGS. 7A-7B, when the user is ready to inject a dose, the user grasps the injection device 10 in his palm with his thumb toward the cap 22. The user than presses the needle guard 14 against his skin causing the needle guard 14 to retract relative to the housing 10 as the needle 18 extends from the opening 14a of the needle guard 14 and into the user's skin.

Figure 8A:
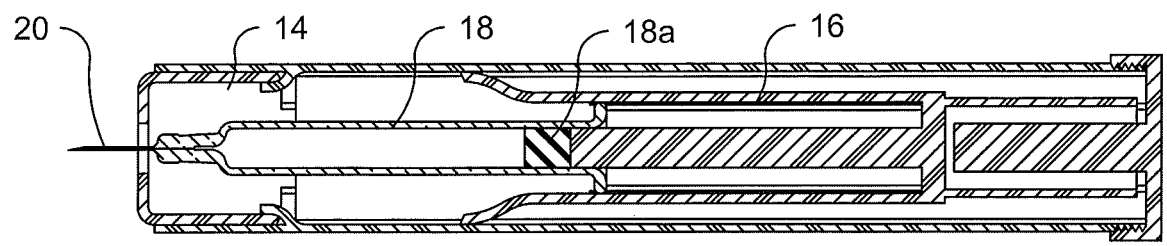
FIG. 8A is a cross sectional view of the injection device of FIG. 1 shown with the needle guard fully retracted and the springs omitted for clarity.
Figure 8B:
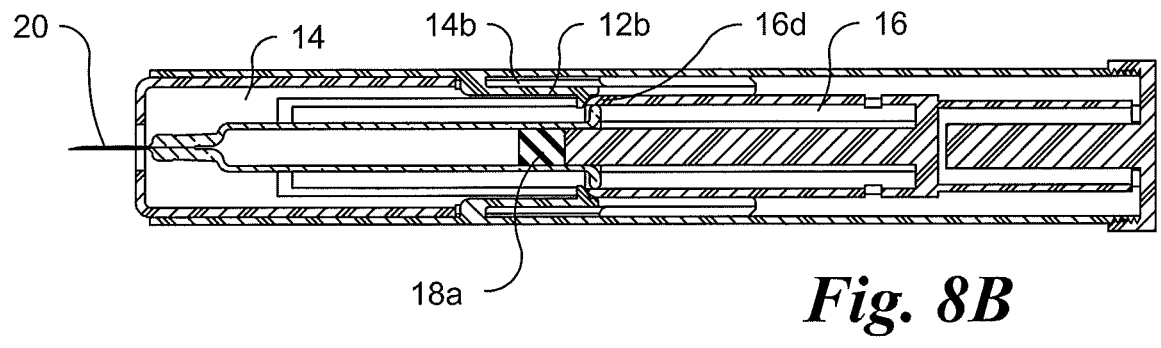
FIG. 8B is a cross sectional view of the injection device of FIG. 1 shown with the needle guard fully retracted and taken 90 degrees from the cross sectional view of FIG. 8A.
Figure 8C:
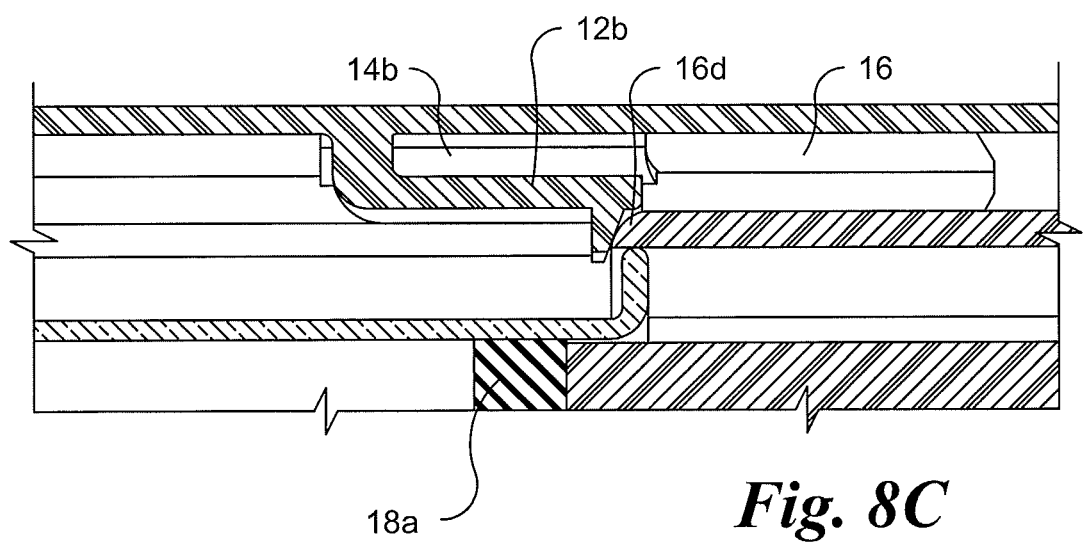
FIG. 8C is an enlarged cross sectional view of the latch shown in FIG. 8B.

Referring to FIGS. 8A-8C, a released position of the injection device may be defined by the at least one retaining arm 12b being clear from the longitudinal path of the ram 16 allowing the ram 16 to extend distally relative to the housing 12. Once the needle 20 is fully inserted into the patient and the needle guard 14 is fully retracted relative to the housing 12, the window 14b of the needle guard 14 aligns with the end of the retaining arm 12b allowing for the retaining arm 12b to flex radially outwardly. As the sloped surface 16d of the ram 16 presses against the retaining arm 12b, the retaining arm 12b flexes into the window 14b, removing the axial retention of the ram 16.

Figure 9A:
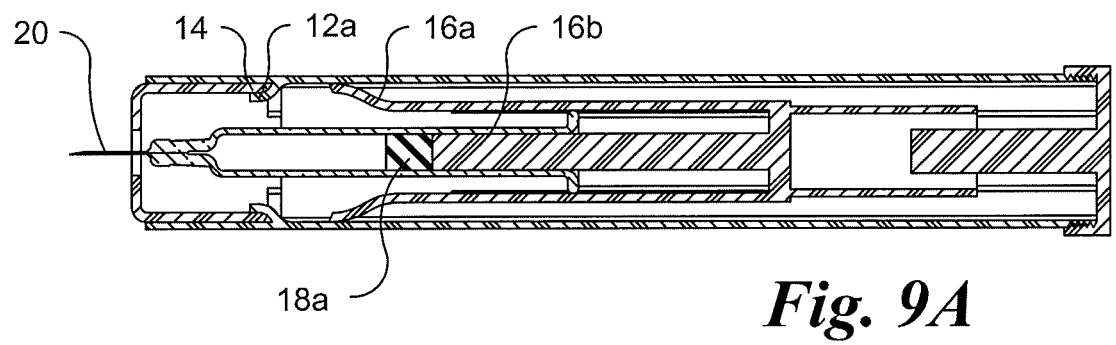
FIG. 9A is a cross sectional view of the injection device of FIG. 1 shown with the ram partially advanced and the springs omitted for clarity.
Figure 9B:
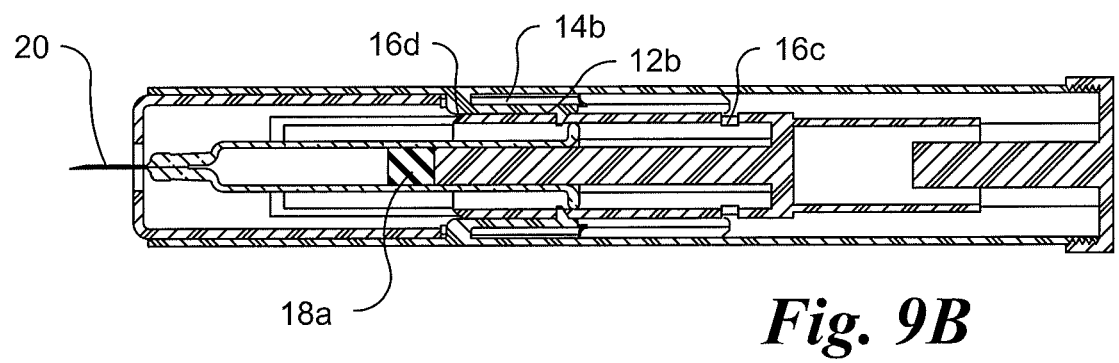
FIG. 9B is a cross sectional view of the injection device of FIG. 1 shown with the ram partially fired and taken 90 degrees from the cross sectional view of FIG. 9A.

Referring to FIGS. 9A-9B, once the retaining arm 12b is flexed out of the longitudinal pathway of the ram 16, the ram 16 is begins to extend distally, causing the rod 16b to move the piston 18a in the syringe 18 distally to expel the medicament from the syringe 18 and into the patient. Note, in FIG. 9B, the retaining arm 12b should be shown flexed outwardly into the window 14b.

Figure 10A:
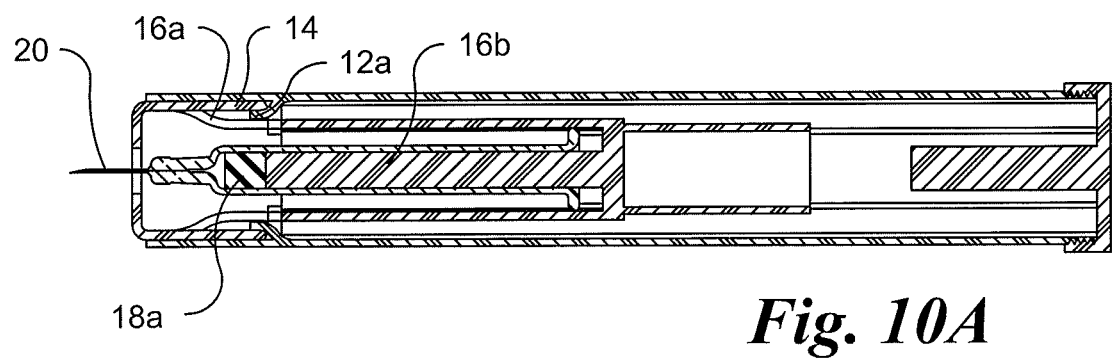
FIG. 10A is a cross sectional view of the injection device of FIG. 1 shown with the ram fully advanced and the springs omitted for clarity.
Figure 10B:
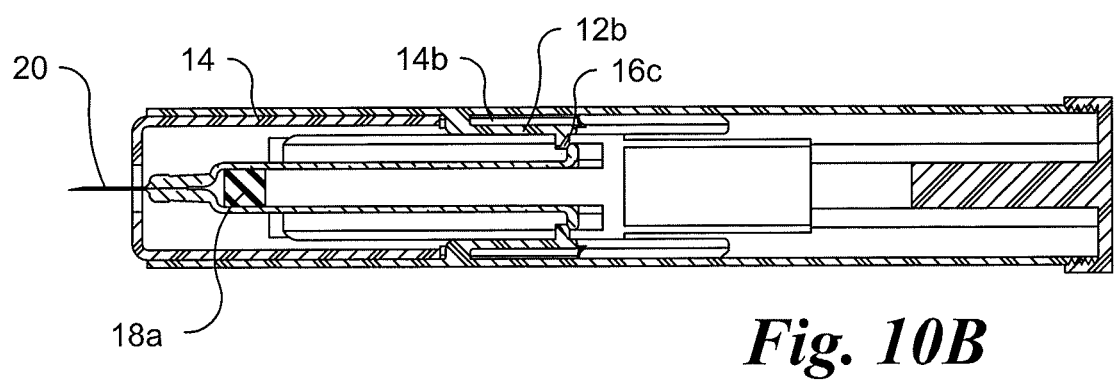
FIG. 10B is a cross sectional view of the injection device of FIG. 1 shown with the ram fully advanced and taken 90 degrees from the cross sectional view of FIG. 10A.

Referring to FIGS. 10A-10B, as the ram 16 extends, the lock arms 16a contact and are flexed inwardly by the hooks 12a of the housing. A portion of the needle guard 14 may extend under the hooks 12a, between the hook 12a and the inner surface of the housing 12. As the ram 16 extends farther, the lock arms 16a overlap a portion of the needle guard 14. Note, in FIG. 10B, the lock arms 16a should be shown flexed inwardly to be contacting the inner surface of the needle guard 14. Once the ram 16 is fully fired or extended, the retaining arm 12b flexes back radially inwardly an into a window 16c of the ram 16 to prevent the ram 16 from being retracted proximally relative to the housing 12.

Figure 11A:
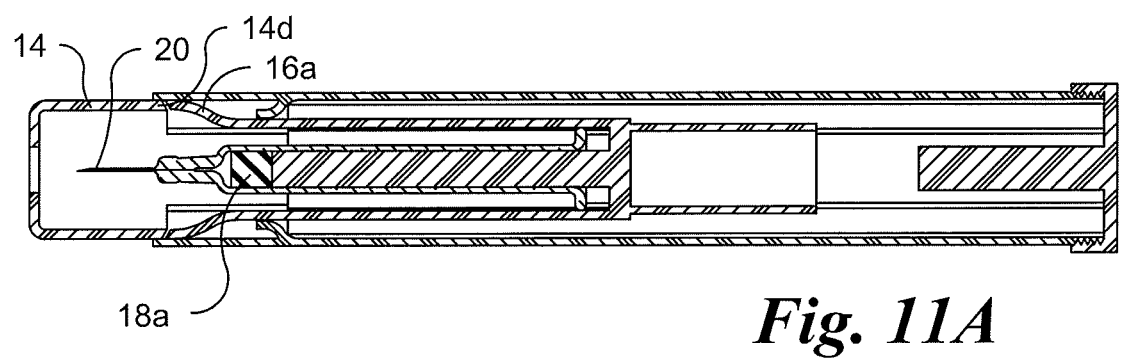
FIG. 11A is a cross sectional view of the injection device of FIG. 1 shown with the needle guard extended and in the locked position and the springs omitted for clarity.
Figure 11B:
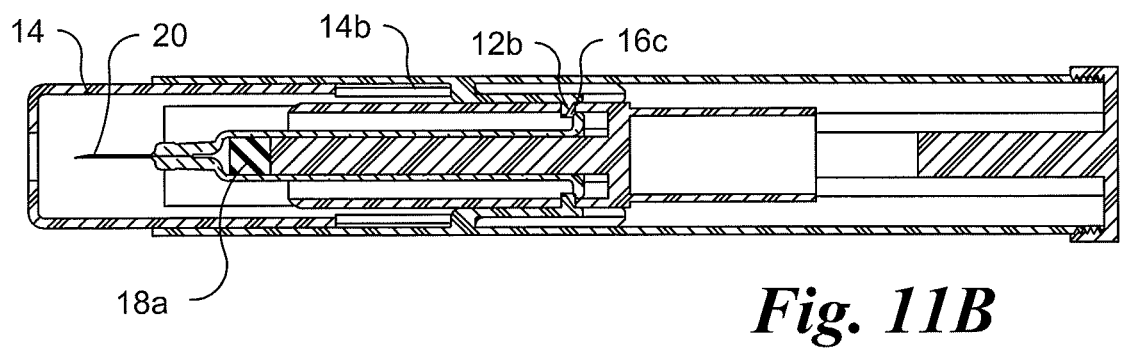
FIG. 11B is a cross sectional view of the injection device of FIG. 1 shown with the needle guard extended and in the locked position and taken 90 degrees from the cross sectional view of FIG. 11A.

Referring to FIGS. 11A-11B, a locked position of the injection device 10 may be defined by the at least one retaining arm 12b being disposed in the longitudinal path of the ram 16 and the at least one lock arm 16a being disposed in the longitudinal path of the needle guard 14 preventing the needle guard 14 from being retracted relative to the housing 12. The needle guard 14 may include a sloped portion 14d configured to engage a sloped end of the lock arm 16a to prevent the lock arm 16a from being pushed radially inwardly and keep the lock arm 16a in the longitudinal path of the needle guard 14. In the locked position, the window 14b of the needle guard 14 is no longer aligned with the retaining arm 12b such that a portion of the needle guard 14 extends between the retaining arm 12b and the inner surface of the housing 12 to prevent the retaining arm 12b from flexing out of the window 16c of the ram 16. Once in the locked position, the injection device 10 is rendered inoperable to prevent reuse or accidental needle sticks. The injection device 10 may then be safely disposed of.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a," "an" and "the" are not limited to one element but instead should be read as meaning "at least one."

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. An injection device for injecting medicament in a patient comprising:
   a housing having at least one retaining arm and at least one retaining rib;
   a syringe coupled to the housing and radially retained relative to the housing by the at least one retaining rib, the syringe having a needle and a piston;
   a needle guard slideably coupled to the housing and spring biased in a distal direction relative to the housing by a return spring;
   a ram slideably coupled to the housing and spring biased in the distal direction relative to the housing by a main spring, the ram having a rod coupled to the piston, the ram having at least one lock arm;
   an initial position defined by the at least one retaining arm being disposed in the longitudinal path of the ram preventing firing of the ram;
   a released position defined by the at least one retaining arm being clear from the longitudinal path of the ram allowing the ram to extend distally relative to the housing; and
   a locked position defined by the at least one retaining arm being disposed in the longitudinal path of the ram and the at least one lock arm being disposed in the longitudinal path of the needle guard preventing the needle guard from being retracted relative to the housing,
   wherein the housing includes at least one hook configured to abut against a portion of the needle guard in the released position and radially flex the at least one lock arm as the lock arm extends distally.

2. The injection device of claim 1, wherein the needle guard includes at least one window and the at least one retaining arm extends through the at least one window.

3. The injection device of claim 2, wherein the needle guard extends between the at least one retaining arm and the housing in the initial and locked positions and the at least one window is aligned with the at least one retaining arm in the released position.

4. The injection device of claim 1, wherein the at least one retaining rib is integral with the housing.

5. The injection device of claim 1, wherein the at least one retaining rib includes four retaining ribs.

6. The injection device of claim 1, wherein the at least one retaining rib includes a radially extending stop configured to abut a bottom surface of a flange of the syringe.

7. The injection device of claim 1, wherein the at least one lock arm is integral with the ram.

8. The injection device of claim 1, wherein the at least one lock arm includes two diametrically opposed lock arms.

9. The injection device of claim 1, wherein the at least one lock arm extends distally further than the rod.

10. The injection device of claim 1, wherein the at least one retaining arm is integral with the housing.

11. The injection device of claim 1, wherein the at least one retaining arm includes two diametrically opposed retaining arms.

12. The injection device of claim 1 further comprising a cap.

13. The injection device of claim 12, wherein the cap includes an extension that extends through the main spring.

14. The injection device of any of claim 1, wherein the return spring abuts against the at least one retaining rib.

15. The injection device of claim 1, wherein the at least one retaining arm includes a cantilever arm that extends in a proximal direction.

16. The injection device of claim 1, wherein the at least one retaining arm includes a radial projection having a sloped surface that abuts a sloped surfaced of the ram in the initial position.

17. The injection device of claim 1, wherein the ram includes at least one window configured to couple with the at least one retaining arm in the locked position.

18. The injection device of claim 1, wherein the injection device consists of the housing, the syringe, the needle, the ram, the needle guard, the return spring, the main spring, and a cap.

19. The injection device of claim 1, wherein the at least one lock arm includes two diametrically opposed lock arms and the at least one retaining arm includes two diametrically opposed retaining arms, each of the two lock arms being circumferentially spaced from each of the two retaining arms.

20. An auto-injector device consisting of:
   a syringe having a needle;
   a housing retaining the syringe;
   a return spring;
   a needle guard slidably coupled to the housing and spring biased relative to the housing by the return spring;
   a main spring;
   a ram slidably coupled to the housing and spring biased relative to the housing by the main spring; and
   a cap coupled to a proximal end of the housing.

21. The injection device of claim 20, wherein a portion of the ram and a portion of the needle guard slide between the syringe and the housing during use.

\* \* \* \* \*